United States Patent
Nakamura et al.

(10) Patent No.: US 7,241,905 B2
(45) Date of Patent: Jul. 10, 2007

(54) DIOXIN ANALOGUES AND METHODS AND KITS FOR SEARCHING OUT DIOXINS-DECOMPOSING ORGANISMS OR ENZYMES OR DIOXIN-DECOMPOSING ENZYME GENES

(75) Inventors: Masaya Nakamura, Ibaraki (JP); Shojiro Hishiyama, Ibaraki (JP)

(73) Assignee: Forestry and Forest Products Research Institute, Ibaraki (JP)

( * ) Notice: Subject to any disclaimer, the term of this patent is extended or adjusted under 35 U.S.C. 154(b) by 56 days.

(21) Appl. No.: 10/472,382

(22) PCT Filed: Mar. 29, 2001

(86) PCT No.: PCT/JP01/02627

§ 371 (c)(1), (2), (4) Date: Sep. 23, 2003

(87) PCT Pub. No.: WO02/076972

PCT Pub. Date: Oct. 3, 2002

(65) Prior Publication Data

US 2004/0115836 A1 Jun. 17, 2004

(30) Foreign Application Priority Data

Mar. 23, 2001 (JP) ............................... 2001-085225

(51) Int. Cl.
- C07D 309/00 (2006.01)
- C12Q 1/00 (2006.01)
- C12Q 1/02 (2006.01)
- G01N 33/569 (2006.01)

(52) U.S. Cl. .................. 549/357; 435/4; 435/7.31; 435/7.32; 435/29

(58) Field of Classification Search ............ 435/4, 435/7.31, 7.32, 29; 549/357
See application file for complete search history.

(56) References Cited

OTHER PUBLICATIONS

Rannug et al. "Use of artifical intellegence in structure-affinity correlations of 2,3,7,8-tetrachlorodibenzo-p-dioxin (TCDD) receptor ligands" Carcinogenesis (1991) 12(11):2007-2015.*

Webster's II New Riverside Dictionary (1994) (Houghton-Mifflin Company: Boston, MA) p. 667.*

Richard C. Cambie et al., "Syntheses of dibenzo [b, e][1,4] dioxinderivatives via iron complexes, and further functionalizations via directed metallation", Journal of Organometallic Chemistry, 420, 1991, pp. 287-418.

Ronald G. Sutherland et al., "Synthesis of some heterocyclic skeletons via organoiron complexes. Crystal and molecular structure of (5a, 6, 7, 8, 9, 9a-eta. 6-1, 4-benzoxathiino [3, 2-b] pyrdiine) (.eta.5-cyclopentadienyl)iron hexafluorophosphate", J. Heterocycl. Chem., 25, 1911, 1998.

M.A. Denomme et al., "Effects of substituents on the cytosolic receptor-binding avidities and aryl hydrocarbon hydroxylase induction potencies of 7-substituted 2,3-dichlorodibenzo-p-dioxins. A quantitative structure-activity relationship analysis", Molecular Pharmacology, 27, pp. 656-661, 1985.

Rebecca D. Prokipcak et al., "7-substituted-2,3-dichlorodibenzo-p-dioxins as competitive ligands for the Ah receptor: quantitative structure-activity relationships (QSARs) and a comparison of human receptor with Ah receptor from rodents", Chemosphere, vol. 20, Nos. 7-9, pp. 1221-1228, 1990.

* cited by examiner

*Primary Examiner*—Leon B. Lankford, Jr.
*Assistant Examiner*—Susan Hanley
(74) *Attorney, Agent, or Firm*—Wenderoth, Lind & Ponack, L.L.P.

(57) ABSTRACT

The present invention provides a novel dioxin analogue for use in the search for organisms capable of degrading dioxin. The dioxin analogue is represented by the following chemical formula (1) or (2):

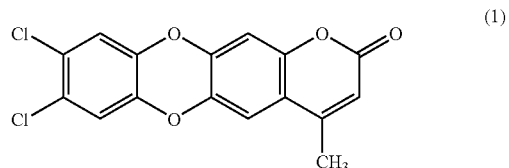

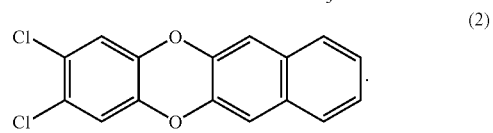

4 Claims, No Drawings

DIOXIN ANALOGUES AND METHODS AND KITS FOR SEARCHING OUT DIOXINS-DECOMPOSING ORGANISMS OR ENZYMES OR DIOXIN-DECOMPOSING ENZYME GENES

This application is a U.S. national stage of International Application No. PCT/JP01/02627 filed Mar. 29, 2001.

TECHNICAL FIELD

The present invention relates to novel dioxin analogues, methods and kits for screening for organisms or enzymes capable of degrading dioxins.

TECHNICAL BACKGROUND

Dioxins are environmental pollutants that have raised public concern because of their toxicity and their ability to remain in the environment for a long time. No practical solution has been proposed so far to effectively eliminate dioxins from the environment. One approach is to collect dioxin-polluted materials in one place for physical and chemical processing. This approach is considered difficult, however, especially when materials contaminated with low-level dioxins are spread over a large area. Bioremediation, a process that takes advantage of biological activities of microbes in cleaning the environment, is currently considered the most effective solution to address such low-level pollution. In constructing an effective bioremediation system, it is crucial to isolate naturally occurring organisms that have a strong ability to rapidly degrade, metabolize, and detoxify dioxins.

Conventional screening processes for dioxin-degrading organisms involve use of dioxins themselves or radioactively labeled other compounds in order to evaluate the ability of organisms to degrade dioxins.

Some of these processes require a pre-treatment in evaluating organisms' capability while others require special instruments to detect radioactively labeled compounds. Also, analytical procedures such as gas chromatography and HPLC employed in these processes are time-consuming.

Accordingly, it is an objective of the present invention to eliminate the above-described drawbacks of the conventional screening techniques for dioxin-degrading organisms by providing a novel screening method that permits even more efficient screening for desired organisms. The present invention also provides compounds and a screening kit for use in this screening process.

DISCLOSURE OF THE INVENTION

In a typical biological breakdown pathway of dioxin utilized by, for example, dibenzo-p-dioxin-degrading fungi, the rate-limiting step is the cleavage of ether bond in the dibenzo-p-dioxin structure, which provides the backbone common among dioxins. The reaction process is as follows:

Terminal dioxygenase

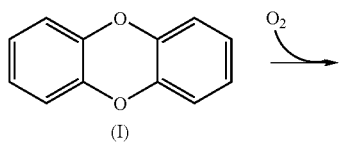

(I)

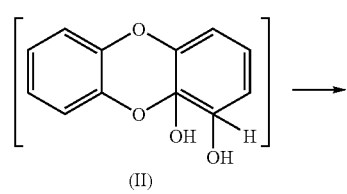

(II)

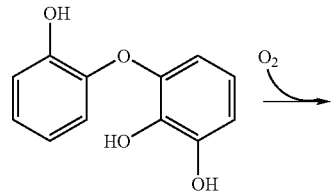

(III)

Extradiol dioxygenase

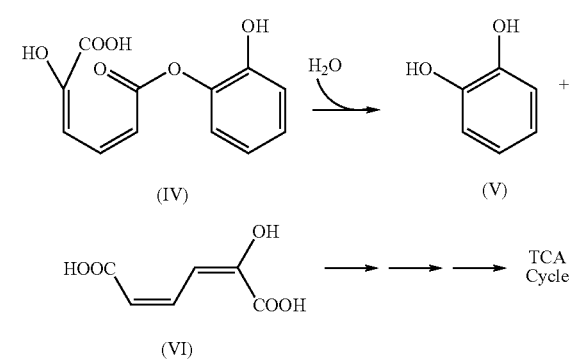

(I) dibenzo-p-dioxin
(II) dibenzo-p-dioxin-cis-dihydrodiol
(III) 2,2',3'-trihydroxydiphenylether
(IV) 2-hydroxy-6-oxo-6-(2-hydroxyphenoxy)-hexa-2,4-dienoate
(V) catechol
(VI) 2-hydroxy-cis, cis-muconic acid The present inventors have directed their interests to the biological breakdown process of dibenzo-p-dioxin shown above and have found that, by substituting one of the benzene rings of dibenzo-p-dioxin with a fluorescent compound having a benzene ring, using this substituted dioxin analogue as a substrate in the same reaction process, and by detecting fluorescence emitted by metabolites, it can easily be determined whether an organism of interest, an enzyme of interest, or a gene encoding an enzyme of interest has an ability to degrade dioxin. This finding ultimately led the present inventors to complete the present invention.

Accordingly, the present invention provides the following items (1) to (10):

(1) A novel dioxin analogue represented by the following chemical formula (1):

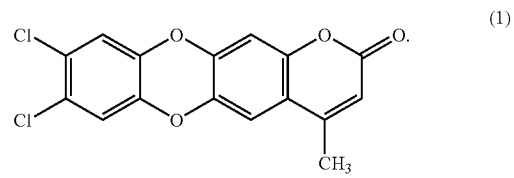

(2) A novel dioxin analogue represented by the following chemical formula (2):

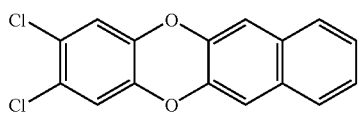
(2)

(3) A method for screening for an organism or an enzyme capable of degrading dioxin, or a gene encoding an enzyme capable of degrading dioxin. The method includes the steps of using a dioxin analogue as a substrate in a reaction involving an organism of interest, an enzyme of interest, or a gene encoding an enzyme of interest; and detecting fluorescence emitted by resulting metabolites. The dioxin analogue is represented by the following general formula (3):

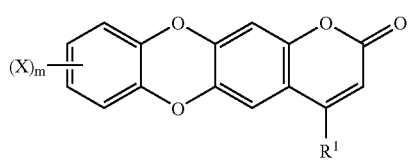
(3)

wherein X represents a chlorine atom, m represents an integer from 1 to 4, and $R^1$ represents a hydrogen atom or a lower alkyl group having 1 to 3 carbon atoms.

(4) The method according to item (3) above, wherein the dioxin analogue represented by the general formula (3) is the dioxin analogue represented by the chemical formula (1):

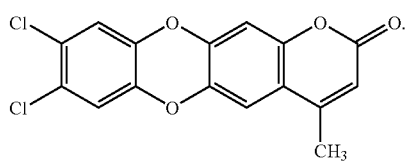
(1)

(5) A method for screening for an organism or an enzyme capable of degrading dioxin, or a gene encoding an enzyme capable of degrading dioxin. The method includes the steps of using a dioxin analogue as a substrate in a reaction involving an organism of interest, an enzyme of interest, or a gene encoding an enzyme of interest; and detecting fluorescence emitted by resulting metabolites. The dioxin analogue is represented by the following general formula

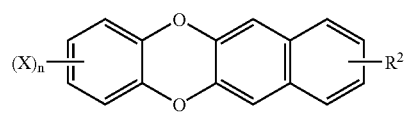
(4)

wherein X represents a chlorine atom, n represents an integer from 1 to 4, and $R^2$ represents a hydrogen atom or a lower alkyl group having 1 to 3 carbon atoms.

(6) The method according to item (5) above, wherein the dioxin analogue represented by the general formula (4) is the dioxin analogue represented by the chemical formula (2):

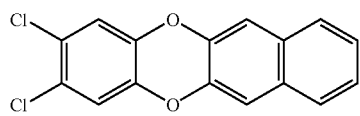
(2)

(7) A screening kit for an organism or an enzyme capable of degrading dioxin, or a gene encoding an enzyme capable of degrading dioxin. The kit includes a dioxin analogue represented by the following general formula (3):

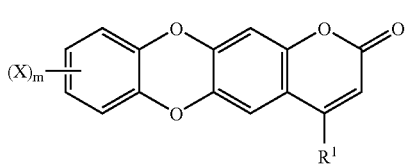
(3)

wherein X represents a chlorine atom, m represents an integer from 1 to 4, and $R^2$ represents a hydrogen atom or a lower alkyl group having 1 to 3 carbon atoms.

(8) The method according to item (7) above, wherein the dioxin analogue represented by the general formula (3) is the dioxin analogue represented by the chemical formula (1):

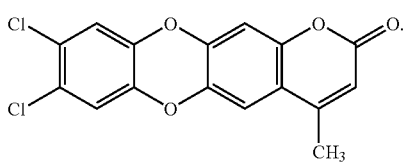
(1)

(9) A screening kit for an organism or an enzyme capable of degrading dioxin, or a gene encoding an enzyme capable of degrading dioxin. The kit includes a dioxin analogue represented by the following general formula (4):

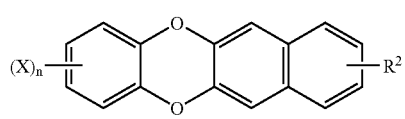
(4)

wherein X represents a chlorine atom, n represents an integer from 1 to 4, and $R^2$ represents a hydrogen atom or a lower alkyl group having 1 to 3 carbon atoms.

(10) The method according to item (9) above, wherein the dioxin analogue represented by the general formula (4) is the dioxin analogue represented by the chemical formula (2):

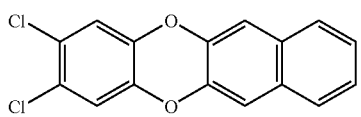
(2)

In the present invention, "dioxins that are degradable by an organism or an enzyme capable of degrading dioxin, or a gene encoding an enzyme capable of degrading dioxin" refer to polychlorodibenzo-p-dioxins, including 2,3,7,8-tetrachlorodibenzo[b,e][1,4]dioxin.

In the present invention, dioxin analogues represented by the chemical formulae (1) and (2) are each a novel compound.

The novel dioxin analogue of the chemical formula (1) can be obtained, for example, by reacting 4-methylesculetin with 1,2,4,5-tetrachlorobenzene in hexamethylphosphoramide (HMPA) solvent in the presence of sodium hydride and a crown ether (18-Crown-6) under inert gas atmosphere.

The novel dioxin analogue of the chemical formula (2) can be obtained, for example, by reacting 2,3-dihidroxynaphthalene with 1,2,4,5-tetrachlorobenzene in hexamethylphosphoramide (HMPA) solvent in the presence of sodium hydride and a crown ether (18-Crown-6) under inert gas atmosphere.

In essence, the method in accordance with the present invention for screening for an organism or an enzyme capable of degrading dioxin, or a gene encoding an enzyme capable of degrading dioxin, makes it possible to determine whether an organism of interest, an enzyme of interest, or a protein encoded by a gene of interest, has an ability to degrade dioxin. This is done by using, as a substrate, a dioxin analogue of the general formula (3) (which is referred to as an esculetin-type dioxin analogue, hereinafter) or a dioxin analogue of the general formula (4) (which is referred to as a naphthalene-type dioxin analogue, hereinafter) in a reaction involving the organism, or the enzyme, or the gene of interest and detecting the fluorescence emitted by the resulting metabolites.

While $R^1$ in the esculetin-type dioxin analogue of the general formula (3) may be any of lower alkyl groups having 1 to 3 carbon atoms, including methyl, ethyl and propyl, the compound preferably has the structure shown by the chemical formula (1).

Similarly, while $R^2$ in the naphthalene-type dioxin analogue of the general formula (4) may be any of lower alkyl groups having 1 to 3 carbon atoms, including methyl, ethyl, and propyl, the compound preferably has the structure shown by the chemical formula (2).

As used herein, the phrase "an organism capable of degrading dioxin" refers to an organism that can catabolize dioxin down to carbon dioxide or can detoxify or alter dioxin through its metabolic system or biological activity.

As used herein, the phrase "an enzyme capable of degrading dioxin" refers to an enzyme that is directly or indirectly involved in the cleavage of the ether bonds in the dioxin structure or is directly or indirectly involved in the dechlorination or hydroxylation of chlorinated dioxins.

As used herein, the phrase "a gene encoding an enzyme capable of degrading dioxin" refers to a gene that codes for the above-described enzyme or a regulatory protein of the enzyme, or any related gene.

As described above, the method of the present invention for screening for an organism or an enzyme capable of degrading dioxin involves using as a substrate the aforementioned esculetin-type dioxin analogue or the naphthalene-type dioxin analogue in a reaction involving an organism or an enzyme of interest and detecting the fluorescence emitted by the metabolites resulting from the degradation process.

Since the products resulting from the cleavage of the ether bonds in the dioxane ring of dioxin analogues (shown below as the chemical formulas (1a), (1b), (2a), (2b) and (2c)) emit fluorescence, they can be used as an index to determine whether an organism of interest has the ability to degrade dioxin.

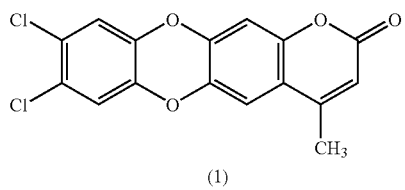

(1)

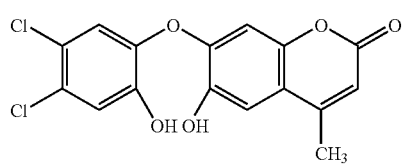

(1a)
Fluorescent

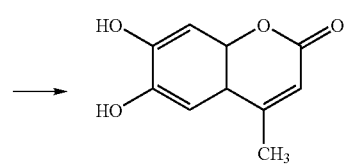

(1b)
Fluorescent

-continued

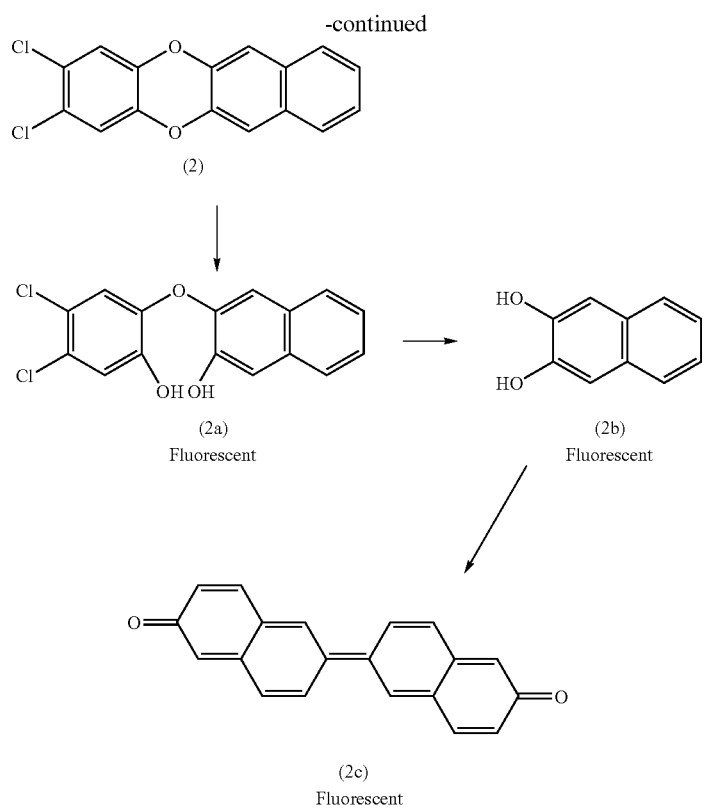

(2)

(2a) Fluorescent (2b) Fluorescent (2c) Fluorescent

Of the degradation products shown in the chemical reactions above, those derived from the esculetin-type dioxin analogue (i.e., chemical formulas (1a) and (1b)) emit fluorescence at 450 to 460 nm when exposed to excitation light of 350 to 380 nm, whereas those derived from the naphthalene-type dioxin analogue (i.e., chemical formulas (2a), (2b) and (2c)) emit fluorescence at 400 to 450 nm when exposed to excitation light of 350 to 360 nm. Thus, an organism of interest can be assayed for the ability to degrade dioxin by irradiating the metabolites, which have resulted from the reaction in which the esculetin-type dioxin analogue or the naphthalene-type dioxin analogue is used as a substrate, either with excitation light with a wavelength of 350 to 380 nm (for esculetin-type dioxin analogue) or with excitation light with a wavelength of 350 to 360 nm (for naphthalene-type dioxin analogue) and detecting the fluorescence at 450 to 460 nm (for esculetin-type dioxin compound) or at 400 to 450 nm (for naphthalene-type dioxin compound). The fluorescence can be detected by, for example, a spectrophotometer. The fluorescence detected at 450 to 460 nm (for esculetin-type dioxin analogue) or at 400 to 450 nm (for naphthalene-type dioxin analogue) indicates that the organism of interest has the ability to degrade dioxin. Alternatively, the metabolites may be visually observed for the emission of fluorescence to screen for an organism capable of degrading dioxin.

In one method of the present invention for screening for an organism capable of degrading dioxin, an organism of interest is cultured in a culture medium added with the above-described substrate (esculetin-type dioxin analogue or naphthalene-type dioxin analogue) dissolved in a small amount of an organic solvent. After culturing for a predetermined period of time, a portion of the supernatant of the culture is collected and is diluted with an alkaline buffer (100 mM glycine, 100 mM sodium hydroxide, pH 10). The collected sample is irradiated with excitation light having a wavelength of 350 to 380 nm (for esculetin-type dioxin analogue) or 350 to 360 nm (for naphthalene-type dioxin analogue) and, using a fluorescence spectrophotometer, fluorescence is detected at 450 to 460 nm (for esculetin-type dioxin analogue) or at 400 to 450 nm (for naphthalene-type dioxin analogue). Alternatively, the fluorescence may be detected using a spectrophotometer. The organic solvent is preferably DMSO, acetone or other water-soluble organic solvents and is preferably added to the culture medium at a concentration not exceeding 1%. When it is desired to add a surfactant to the culture medium, the substrate is dissolved in a water-insoluble organic solvent such as nonane or hexane and is preferably added to the culture medium such that the final concentration of the surfactant does not exceed 1%. The medium is thoroughly mixed to disperse the substrate.

In one method of the present invention for screening for an enzyme capable of degrading dioxin, the present substrate dissolved in a buffer (pH 4 to 7) is placed in a glass test tube along with a crude enzyme (crude extract) or a fractionated enzyme obtained from an organism suspected of having the ability to degrade dioxin, and the reaction is allowed to proceed for a predetermined period of time. Subsequently, some or all of the reaction mixture is transferred to another glass test tube and is diluted with an alkaline buffer (100 mM glycine, 100 mM sodium hydroxide, pH 10). The mixture is then transferred to a silica cell for fluorescence analysis and is irradiated with excitation light having a wavelength of 350 to 380 nm (for esculetin-type dioxin analogue) or 350 to 360 nm (for naphthalene-type dioxin analogue). Using a fluorescence spectrophotometer, fluorescence is detected at 450 to 460 nm (for esculetin-type dioxin analogue) or at 400 to 450 nm (for naphthalene-type dioxin analogue). Alternatively, the coloring of the solution may be detected using a spectrophotometer. The organic solvent is preferably DMSO, acetone or other water-soluble organic solvents and is preferably added to the reaction solution at a concentration not exceeding 1%. When it is desired to add a surfactant to the reaction solution, the substrate is dissolved in a water-insoluble organic solvent such as nonane or hexane and is preferably added to the culture medium such that the final concentration of the surfactant does not exceed 1%. The solution is thoroughly mixed to disperse the substrate.

In one method of the present invention for screening for a gene encoding an enzyme capable of degrading dioxin, a gene library of an organism expressing the ability to degrade dioxin is introduced into a bacterium, such as *E. Coli*, or a eukaryotic microorganism, such as yeast, which is incapable of degrading dioxin. These transformants are then screened according to the above-described method to identify the gene involved in the degradation process of dioxin.

The kit of the present invention for screening for an organism or an enzyme capable of degrading dioxin, or a gene encoding an enzyme capable of degrading dioxin, is characterized in that it includes the esculetin-type dioxin analogue of the general formula (3) or the naphthalene-type dioxin analogue of the general formula (4).

The screening kit is adapted to implement the above-described method for screening for an organism or an enzyme capable of degrading dioxin or a gene encoding an enzyme capable of degrading dioxin and includes an esculetin-type dioxin analogue or a naphthalene-type dioxin analogue in a crystallized form to serve as a substrate, an organic solvent (DMSO or acetone) for dissolving the substrate, and an alkaline buffer (100 mM glycine, 100 mM sodium hydroxide, pH 10) used in the detection of the fluorescence. The kit is used according to the procedure described in the foregoing paragraph.

BEST MODE FOR CARRYING OUT THE INVENTION

EXAMPLE 1

0.19 g (11.0 mM) 4-methylesculetin, 0.072 g (1.8 mM) sodium hydride (60% suspension in oil), and 0.476 g (1.8 mM) crown ether (18-Crown-6) were admixed with 4 ml hexamethylphosphoramide (HMPA) at room temperature under nitrogen atmosphere. The mixture was thoroughly mixed until the solutes dissolved completely. Subsequently, 0.108 g (0.5 mM) 1,2,4,5-tetrachlorobenzene was added to the mixture and the mixture was stirred at 50° C. to completely dissolve the solute. After dissolving, the reaction was allowed to proceed for 3 hours at 120° C. The reaction was constantly monitored by thin-layer chromatography (developing solvent, ethyl acetate:n-hexane=1:3). Upon completion of the reaction, the reaction mixture was allowed to cool to room temperature and was diluted with 50 mL ethyl acetate, followed by washing 3 times with saturated brine. The organic layer was then concentrated under reduced pressure. The resulting concentrate was purified by silica gel column chromatography (eluant, ethyl acetate:n-hexane=1:3) to obtain 0.12 g of the desired compound as an oily product. The oily product was then crystallized with chloroform and hexane to give 86 mg of the crystallized compound of the chemical formula (1). The physical properties of the resulting compound are as follows:

mp: 296-298° C. $^1$H-NMR ($\delta$: ppm) [CDCl$_3$] 2.34 (3H, s), 6.19 (1H, s), 6.82 (1H, s), 6.96 (1H, s), 6.99 (1H, s), 7.02 (1H, s) $^{13}$C-NMR ($\delta$: ppm) [CDCl$_3$] 18.7, 105.1, 111.1, 114.0, 116.3, 117.8, 118.0, 127.1, 127.5, 137.9, 139.8, 140.4, 143.9, 150.5, 160.4

EXAMPLE 2

0.16 g (11.0 mM) 2,3-dihydroxynaphthalene, 0.072 g (1.8 mM) sodium hydride (60% suspension in oil), and 0.476 g (1.8 mM) crown ether (18-Crown-6) were admixed with 4 ml hexamethylphosphoramide (HMPA) at room temperature under nitrogen atmosphere. The mixture was thoroughly mixed until the solutes dissolved completely. Subsequently, 0.108 g (0.5 mM) 1,2,4,5-tetrachlorobenzene was added to the mixture and the mixture was stirred at 50° C. to completely dissolve the solute. After dissolving, the reaction was allowed to proceed for 3 hours at 130° C. The reaction was continuously monitored by thin-layer chromatography (developing solvent, ethyl acetate:n-hexane=1:3). Upon completion of the reaction, the reaction mixture was allowed to cool to room temperature and was diluted with 50 mL ethyl acetate, followed by washing 3 times with saturated brine. The organic layer was then concentrated under reduced pressure. The resulting concentrate was purified by silica gel column chromatography (eluant, ethyl acetate:n-hexane=1:3) to obtain 0.098 g of the desired compound as an oily product. The oily product was then crystallized with hexane to give 68 mg of the crystallized compound of the chemical formula (2). The physical properties of the resulting compound are as follows:

mp: 136-138° C. $^1$H-NMR ($\delta$: ppm) [CDCl$_3$] 7.03 (2H, s), 7.24 (2H, s), 7.34 (1H, s), 7.35 (1H, s), 7.63 (1H, s), 7.64 (1H, s) $^{13}$C-NMR ($\delta$: ppm) [CDCl$_3$] 112.5, 117.8, 125.7, 126.5, 126.9, 131.0, 140.6, 140.7

EXAMPLE 3

Different species of wood-rotting fungi (i.e., *Grammothele fuligo* WD844, *Phanerochaete crassa* WD1694, *Phanerochaete chrysosporium* ME446, *Fomitopsis palustris*, *Coriolus versicolor*, and *Pleurotus pulumonairus*) were used as test subjects and were screened for the ability to degrade the dioxin analogue obtained in Example 1 (esculetin-type analogue).

Each subject fungal species, which had been pre-cultured on potato agar and stamped out of the agar using a cork borer, was inoculated onto 10 ml modified NS medium (3% glucose, 1% peptone, inorganic salts, pH 5.0) in a 100 ml Erlenmeyer flask and was cultured for 5 to 7 days at 28° C. Subsequently, a 100 µl DMSO solution containing the substrate (esculetin-type dioxin analogue obtained in Example 1) at a final concentration of 1 ppm was added to the culture. The solution was added so that the concentration of DMSO in the medium was 1%. Samples of the culture solution were collected at predetermined time intervals (i.e., 1, 3, and 5 days after the addition of the substrate). To a 100 µl portion of each sample, 1.9 ml of an alkaline buffer (100 mM glycine, 100 mM sodium hydroxide, pH 10.0) was added. The sample mixtures were then exposed to long-range UV light (365 nm) as excitation light and were visually screened for those emitting fluorescence. On day 7, the samples were irradiated with excitation light of 350 nm and, using a fluorescence spectrophotometer, the intensity of fluorescence was measured at 450 nm. The results are shown in Table 1 below. A control shown in Table 1 is the above-described culture medium with only dioxin analogue (esculetin-type) added.

TABLE 1

| Subject Fungi | Fluorecsence intensity |
| --- | --- |
| Control | 1370 |
| G. fuligo WD844 | 1639 |
| P. crassa WD1694 | 1419 |
| P. pulumonairus | 2203 |
| F. palustris | 1314 |
| C. versicolor | 1601 |
| P. chrysosporium | 1619 |

As shown by the results above, Pleurotus pulumonairus caused the most significant fluorescence emission, followed by WD844 (Grammothele fuligo), ME446 (Phanerochaete chrysosporium), and then Coriolus versicolor. Pleurotus pulumonairus was found to cause more intense fluorescence than did ME446 (Phanerochaete chrysosporium), a wood-rotting fungus known for its ability to degrade dioxin.

EXAMPLE 4

Different species of wood-rotting fungi (i.e., Grammothele fuligo WD844, Phanerochaete crassa WD1694, Phanerochaete chrysosporium ME446, Fomitopsis palustris, Coriolus versicolor, and Pleurotus pulumonairus) were used as test subjects and were screened for the ability to degrade the dioxin analogue obtained in Example 2 (naphthalene-type analogue).

Each subject fungal species, which had been pre-cultured on potato agar and stamped out of the agar using a cork borer, was inoculated onto 10 ml modified NS medium (3% glucose, 1% peptone, inorganic salts, pH5.0) in a 100 ml Erlenmeyer flask and was cultured for 5 to 7 days at 28° C. Subsequently, a 100 µl DMSO solution containing the substrate naphthalene-type dioxin analogue obtained in Example 2 at a final concentration of 1 ppm was added to the culture. The solution was added so that the concentration of DMSO in the medium was 1%. Samples of the culture solution were collected at predetermined time intervals (i.e., 1, 3, and 5 days after the addition of the substrate). To a 100 µportion of each sample, 1.9 ml of an alkaline buffer (100 mM glycine, 100 mM sodium hydroxide, pH10.0) was added. The sample mixtures were then exposed to long-range UV light (365 nm) as excitation light and were visually screened for those emitting fluorescence. As a result, it was proven that Pleurotus pulumonairus caused the most intense fluorescence emission than the other species of the wood rotting fungi tested.

REFERENCE EXAMPLE 1

Pleurotus pulumonairus, which has proven to cause the most intense fluorescence in Examples 3 and 4, was examined for its ability to degrade dioxin.

As in Examples 3 and 4, Pleurotus pulumonairus was cultured in a culture medium containing glucose and peptone and, on day 7, 2,3,7,8-tetrachlorodioxin was added to the medium at a final concentration of 0.5 ppm. The fungus was subsequently cultured for 20 days. After the culturing period, the culture medium containing the fungus was freeze-dried and was subjected to extraction by refluxing with hexane. Hexane was then removed by distillation and the remaining culture was diluted 200-fold with 200 ml methanol containing 100 ppm Triton X-100. Using a High Performance Dioxin Immunoassay Kit (Cape Technologies, United States) according to the manufacturer's instruction, the concentration of dioxin was measured to determine the degradation rate of dioxin. The results are shown in Table 2 below. A control shown in Table 2 is the above-described culture medium with only 2,3,7,8-tetrachlorodioxin added. Fomitopsis palustris was used as a negative control.

TABLE 2

| Fungus | Degradation rate |
| --- | --- |
| Control | 0% |
| Pleurotus pulumonairus | 31% |
| Fomitopsis palustris | 9% |

As can be seen from the results of Table 2, Pleurotus pulumonairus, which has proven to cause the most intense fluorescence in Examples 3 and 4, showed a significant ability to degrade dioxin. The 9% degradation rate observed for Fomitopsis palustris, which is incapable of degrading dioxin, is considered to have resulted from non-specific binding of dioxin to the fungal cells, rather than from the degradation of dioxin.

INDUSTRIAL APPLICABILITY

The present invention allows rapid, simple, and highly sensitive screening for organisms that can degrade, metabolize, and detoxify dioxins rapidly and effectively and can thus be applicable to the bioremediation of the environment. The present invention therefore enables construction of highly effective bioremediation system that helps eliminate the problem of dioxin contamination, a problem increasingly becoming an issue of public concern.

Furthermore, the present invention allows biochemical analysis (enzymatic-chemical, kinetic, or molecular biological analysis) of degradative/metabolic systems of dioxins in living organisms, thereby making it possible to accumulate fundamental data on molecular evolution required for the purposes of developing novel bio-reactors for cleaning the environment and designing high-performance degradative enzymes by protein engineering.

What is claimed is:

1. A novel dioxin analogue which is formula (1):

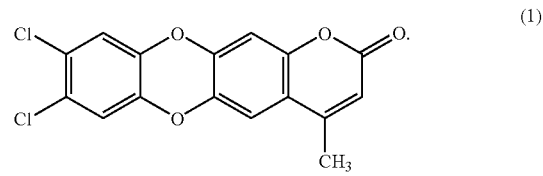

(1)

2. A method for screening for an organism or an enzyme capable of degrading dioxin, or a gene encoding an enzyme capable of degrading dioxin, comprising the steps of contacting the dioxin analogue according to claim 1 as a substrate in a reaction with a composition comprising a cell culture of an organism of interest, an enzyme of interest, or a cell culture of a recombinant organism having a gene encoding an enzyme of interest to form a reaction mixture; and detecting the fluorescence emitted by the fluorescent metabolites resulting from the reaction of said dioxin analogue with said composition.

3. A method for screening for an organism or an enzyme capable of degrading dioxin, or a gene encoding an enzyme capable of degrading dioxin, comprising the steps of contacting a dioxin analogue as a substrate in a reaction with a composition comprising a cell culture of an organism of interest, an enzyme of interest, or a cell culture of a recombinant organism having a gene encoding an enzyme of interest to form a reaction mixture; and detecting the fluorescence emitted by the fluorescent metabolites resulting from the reaction of said dioxin analogue with said composition, wherein the dioxin analogue is formula (3):

(3)

wherein X is a chlorine atom, m is an integer from 1 to 4, and $R^1$ is a hydrogen atom or a lower alkyl group having 1 to 3 carbon atoms.

4. A screening kit for an organism or an enzyme capable of degrading dioxin, or a gene encoding an enzyme capable of degrading dioxin, the kit comprising a dioxin analogue which is the following general formula (3):

(3)

wherein X is a chlorine atom, m is an integer from 1 to 4, and $R^1$ is a hydrogen atom or a lower alkyl group having 1 to 3 carbon atoms.

* * * * *